United States Patent
Sholder

(10) Patent No.: US 9,177,459 B2
(45) Date of Patent: *Nov. 3, 2015

(54) ECG-ENABLED PERSONAL EMERGENCY RESPONSE SYSTEMS

(71) Applicant: Jason A. Sholder, Edgewater, NJ (US)

(72) Inventor: Jason A. Sholder, Edgewater, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/691,717

(22) Filed: Apr. 21, 2015

(65) Prior Publication Data

US 2015/0228176 A1 Aug. 13, 2015

Related U.S. Application Data

(63) Continuation of application No. 13/886,095, filed on May 2, 2013, now Pat. No. 9,019,100.

(60) Provisional application No. 61/732,013, filed on Nov. 30, 2012, provisional application No. 61/688,466, filed on May 16, 2012.

(51) Int. Cl.
| G08B 1/08 | (2006.01) |
|---|---|
| G08B 21/02 | (2006.01) |
| G08B 25/00 | (2006.01) |
| G08B 25/01 | (2006.01) |
| A61B 5/00 | (2006.01) |
| A61B 5/0404 | (2006.01) |
| A61B 5/11 | (2006.01) |

(Continued)

(52) U.S. Cl.
CPC .......... *G08B 21/0211* (2013.01); *A61B 5/0006* (2013.01); *A61B 5/0022* (2013.01); *A61B 5/044* (2013.01); *A61B 5/0404* (2013.01); *A61B 5/0432* (2013.01); *A61B 5/04085* (2013.01); *A61B 5/1112* (2013.01); *A61B 5/6843* (2013.01); *A61B 5/6898* (2013.01); *A61B 5/746* (2013.01); *A61B 5/747* (2013.01); *A61B 5/7415* (2013.01); *A61B 5/7475* (2013.01); *G08B 21/02* (2013.01); *G08B 21/0269* (2013.01); *G08B 21/0283* (2013.01); *G08B 21/043* (2013.01); *G08B 21/0446* (2013.01); *G08B 25/001* (2013.01); *G08B 25/016* (2013.01); *A61B 5/1117* (2013.01); *A61B 2560/0468* (2013.01); *A61B 2562/0219* (2013.01)

(58) Field of Classification Search
CPC .............................. G08B 21/0211; G08B 21/02
USPC .................. 340/539.12, 539.13; 600/300, 301
See application file for complete search history.

(56) References Cited

U.S. PATENT DOCUMENTS

| 5,010,893 A | 4/1991 | Sholder |
|---|---|---|
| 5,348,008 A | 9/1994 | Bornn et al. |

(Continued)

OTHER PUBLICATIONS

PCT/US2013/039332, International Search Report and Written Opinion of the International Searching Authority, Aug. 29, 2013.

*Primary Examiner* — Eric Blount
(74) *Attorney, Agent, or Firm* — Paul Diamond, Esq.; Diamond Law Office, LLC

(57) ABSTRACT

The invention provides personal emergency response systems (PERS) with expanded life-saving capabilities. One embodiment of the invention provides a wearable PERS pendant that incorporates a cell phone transmitter or transceiver, a GPS location system, an accelerometer-based fall detector that automatically triggers an alert, and an electrocardiogram (ECG) recorder permitting a remote service center or medical personnel to receive and respond to transmitted alerts and electrocardiographic data.

20 Claims, 8 Drawing Sheets

(51) Int. Cl.
*G08B 21/04* (2006.01)
*A61B 5/0408* (2006.01)
*A61B 5/0432* (2006.01)
*A61B 5/044* (2006.01)

(56) References Cited

U.S. PATENT DOCUMENTS

| | | | |
|---|---|---|---|
| 5,509,927 A | 4/1996 | Epstein et al. | |
| 5,564,429 A | 10/1996 | Bornn et al. | |
| 5,708,417 A | 1/1998 | Tallman et al. | |
| 5,959,529 A | 9/1999 | Kail | |
| 5,961,446 A | 10/1999 | Beller et al. | |
| 6,160,478 A | 12/2000 | Jacobsen et al. | |
| 6,175,308 B1 | 1/2001 | Tallman et al. | |
| 6,269,264 B1 | 7/2001 | Weyant et al. | |
| 6,364,834 B1 * | 4/2002 | Reuss et al. | 600/300 |
| 6,486,779 B1 | 11/2002 | Alroy | |
| 6,608,559 B1 | 8/2003 | Lemelson et al. | |
| 6,622,045 B2 | 9/2003 | Snell et al. | |
| 6,783,492 B2 * | 8/2004 | Dominguez et al. | 600/365 |
| 6,819,247 B2 | 11/2004 | Birnbach | |
| 6,934,587 B1 | 8/2005 | Bornzin et al. | |
| 7,185,282 B1 | 2/2007 | Naidoo et al. | |
| 7,233,827 B1 | 6/2007 | Bornzin et al. | |
| 7,285,090 B2 * | 10/2007 | Stivoric et al. | 600/300 |
| 7,420,472 B2 * | 9/2008 | Tran | 340/573.1 |
| 7,586,418 B2 | 9/2009 | Cudihy et al. | |
| 7,733,224 B2 * | 6/2010 | Tran | 340/540 |
| 8,112,149 B2 | 2/2012 | Sholder | |
| 2002/0032386 A1 * | 3/2002 | Sackner et al. | 600/536 |
| 2004/0167417 A1 * | 8/2004 | Schulhauser et al. | 600/513 |
| 2004/0246128 A1 | 12/2004 | Menard | |
| 2005/0115561 A1 * | 6/2005 | Stahmann et al. | 128/200.24 |
| 2008/0001735 A1 | 1/2008 | Tran | |
| 2009/0048540 A1 | 2/2009 | Otto | |
| 2009/0069724 A1 | 3/2009 | Otto | |
| 2011/0115624 A1 | 5/2011 | Tran | |
| 2011/0181422 A1 | 7/2011 | Tran | |
| 2012/0092156 A1 | 4/2012 | Tran | |
| 2012/0092157 A1 | 4/2012 | Tran | |

* cited by examiner

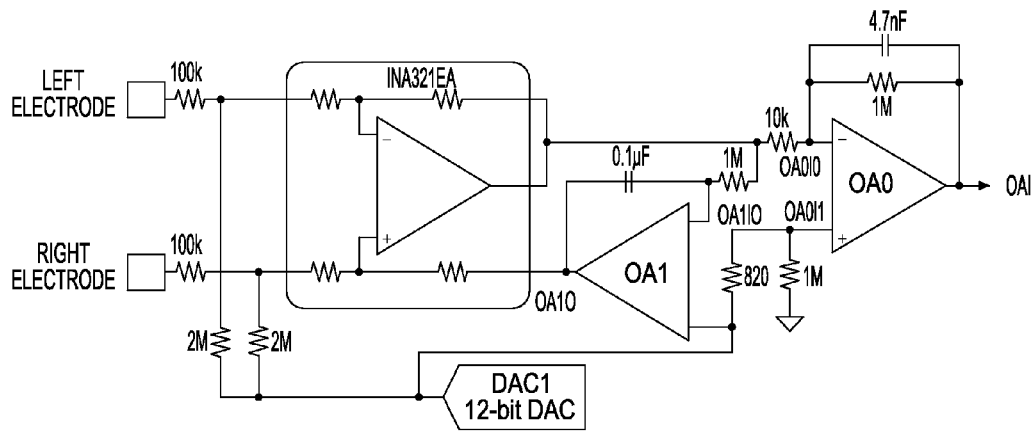
FIG. 6
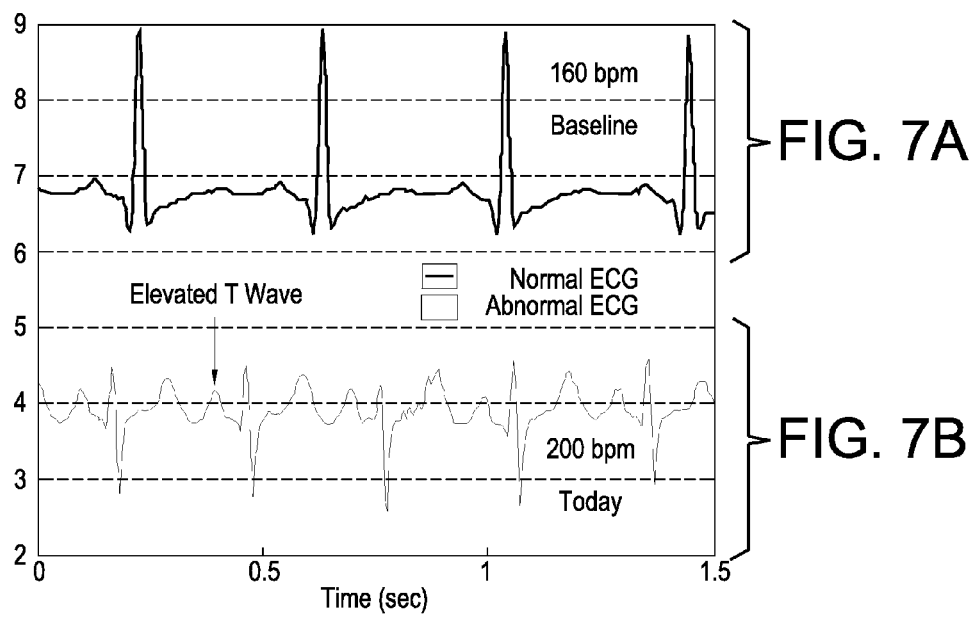
FIG. 7A
FIG. 7B

ECG-ENABLED PERSONAL EMERGENCY RESPONSE SYSTEMS

CROSS-REFERENCE TO RELATED APPLICATIONS

This application is a continuation of U.S. application Ser. No. 13/886,095 filed May 2, 2013 (now U.S. Pat. No. 9,019, 100), which claims the benefit of U.S. provisional application Ser. Nos. 61/732,013 filed Nov. 30, 2012 and 61/688,466 filed May 16, 2012, each of the aforementioned applications hereby incorporated by reference herein in its entirety.

FIELD OF THE INVENTION

The invention relates to the field of personal emergency response systems (PERS).

BACKGROUND

Typical personal emergency response systems consist of a pendant worn by a user who may initiate an emergency call by actuating a button on the pendant, thereby causing a signal to be transmitted to a dedicated base station located in the user's home. In response, the base station dials an emergency call center (call monitoring center) via a telephone line and the user can talk to an attendant via a speaker-phone built into the base station or pendant. In response to a request therefor by the user, or in response to failure of the user to respond to inquiries from call center personnel, emergency assistance is dispatched by the call center to the user's location.

What is needed and provided by the present invention are personal emergency response systems with expanded life-saving capabilities.

SUMMARY OF THE INVENTION

One embodiment of the invention provides a personal emergency response system apparatus that includes:
  a portable housing sized and configured to be hand carried, held in pocket, or removably attached to a human user or clothing worn by the user;
  at least one processor;
  processor-accessible memory;
  processor-implementable computer instructions stored in the processor-accessible memory;
  a wireless transmitter or transceiver, such as a cellular telephone transmitter or cellular telephone transceiver, operably linked to the processor;
  an electrocardiographic monitoring circuit operably linked to the processor;
  electrocardiographic monitoring electrodes operably connected to the electrocardiographic monitoring circuit, said electrodes being at least partially externally disposed (with respect to the housing) for contact with the user's body; and
  a manual alert button operably linked to the processor,
  wherein the at least one processor, the processor-accessible memory, the transmitter or transceiver and the electrocardiographic monitoring circuit are disposed within the housing, and
    wherein said computer instructions are configured to direct the at least one processor to perform the steps of:
      transmitting the electrocardiographic data obtained from a user using the apparatus to at least one preselected remote recipient, such as a PERS call service center, using the transmitter or transceiver, and
      in response to operation of the manual alert button, transmitting an emergency alert message to at least one preselected remote recipient, such as a PERS call service center and/or a 911 emergency call center, using the transmitter or transceiver.

The invention also provides methods for obtaining reference (baseline) electrocardiographic data of the user using such an apparatus and storing said data for comparison to electrocardiographic data that is later obtained from the user using the apparatus, for example, under putative emergency conditions.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

FIG. 6 shows an electrocardiographic monitoring circuit that may be used in a PERS apparatus embodiment of the invention.

FIGS. 7A and 7B shows sample digitized output of an electrocardiographic monitoring circuit that may be used in a PERS device embodiment of the invention with "normal" baseline reference data (FIG. 7A) and abnormal (elevated T wave) data (FIG. 7B).

DETAILED DESCRIPTION

The invention provides improved personal emergency response systems and related apparatuses with expanded capabilities. Use of the system and its devices is geared primarily toward the elderly who are living alone and are concerned that if they fall and injure themselves, they will be unable to recover themselves or request emergency assistance. These people can avail themselves of existing PERS systems in which they are provided a wearable personal transmitter that, when activated, transmits a signal to a home unit that calls the PERS provider for help. However, the fact remains that many seniors who wear or are candidates for PERS pendants may be mobile and not relegated to being at home when and if they fall, or may need emergency assistance for reasons other than a fall such as in the event of an adverse cardiac event. Thus, commercially available wearable PERS transmitters that do not work outside the home have limited utility.

The present invention provides wearable PERS transmitters or transceivers that allow the user to be "covered" away from home while also providing additional PERS capabilities. In addition, in contrast to a conventional, home-based PERS system where technicians already know the home address of the user, systems of the invention may include location identification and transmission, for example, using built-in GPS, so that a user's location away from the home can be determined and emergency personnel dispatched accordingly. In practice, the call monitoring center with which the PERS user device communicates may be provided access to the user's home address and the user's/pendant's precise geographic location.

Without limitation, one embodiment of a portable PERS device according to the invention provides a combination of the following functions and features: (1) manual and automatic alert initiation and transmission; (2) intelligent fall detection for automatic fall alert initiation and transmission; (3) mobility outside of the home/living quarters with address and/or geographic location determination and transmission; (4) two-way voice and data communication; and (5) ECG electrocardiographic rhythm strip recording via integrated ECG electrodes and circuitry.

Figure 1:
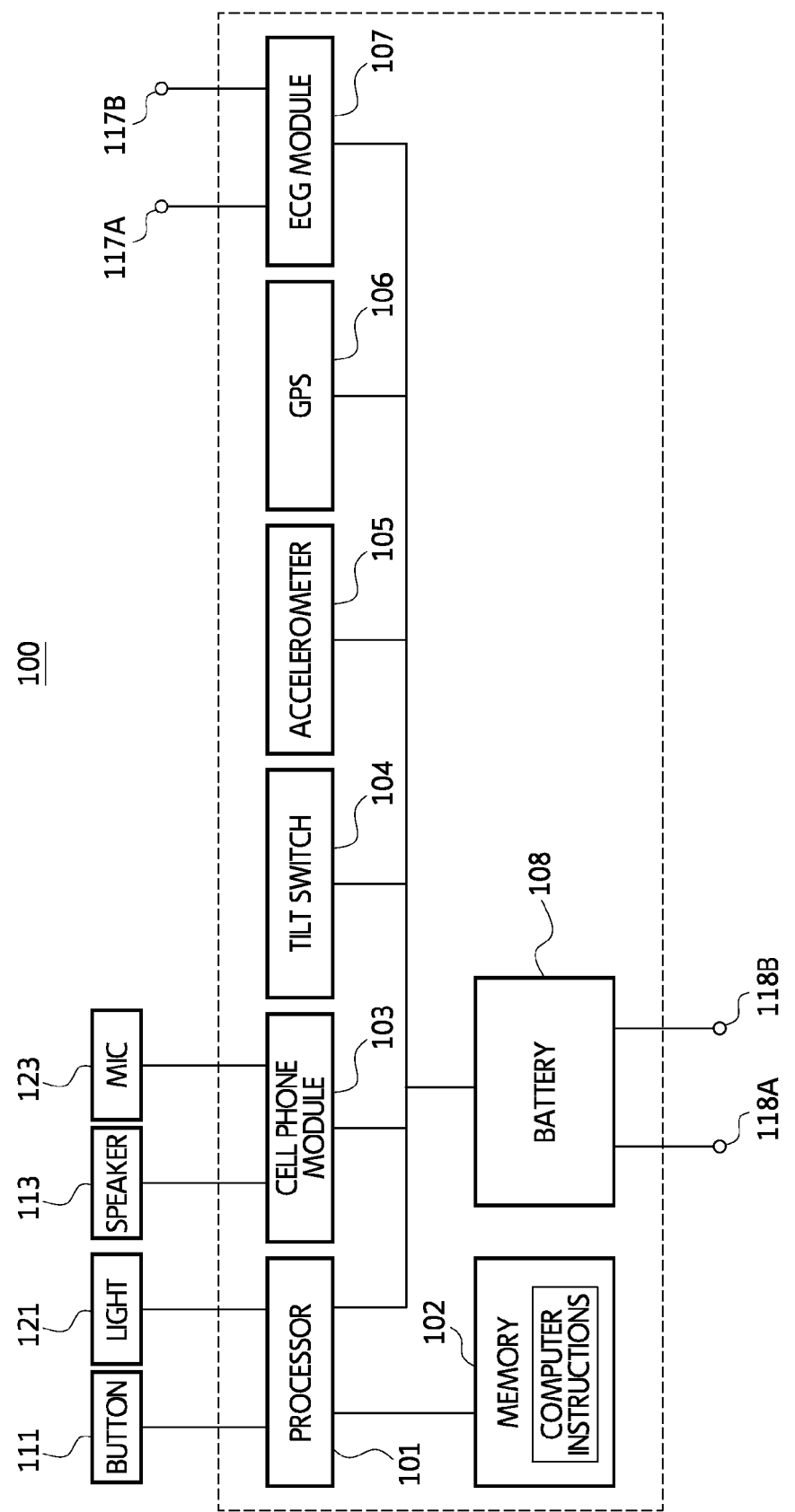
FIG. 1 is a schematic diagram showing the components of a PERS apparatus embodiment of the invention.

FIG. 1 is a schematic diagram showing the various components of a PERS apparatus/pendant embodiment 100 of the invention. The PERS apparatus/pendant includes a housing that encloses and/or presents various components including at least one processor 101 (computer processor, i.e., a microprocessor) and operably linked thereto (directly or indirectly): computer accessible memory 102, computer instructions recorded in the computer accessible memory said instructions configured to direct the processor to carry out the various functions of the PERS apparatus/pendant in concert with and by controlling the various hardware components of the device; a cellular telephone module 103 capable of sending and receiving voice and/or other data via at least one cellular telephone network; a speaker 113; a microphone 123; an optional tilt switch 104 to monitor orientation (standing/vertical or laying/horizontal); an accelerometer 105 such as a 3-axis accelerometer to monitor fall detection and/or user movement/motion generally in conjunction with the processor and computer instructions therefor; a press button 111 configured to initiate a call/alert and/or cancel a call/alert upon actuating the button; an indicator light 121 such as a light emitting diode; and an electrocardiogram (ECG) circuit module 107 operably connected to two ECG electrodes 117A and 117B disposed (at least partially) on the exterior of the monitor/pendant so that the ECG electrodes may be contacted with the user's body to obtain an electrocardiogram or electrocardiographic rhythm recording. The PERS monitor of the embodiment also includes a rechargeable battery 108 for powering the device and its various components, exterior accessible electrical contacts 118A and 118B for charging the battery such as electrodes for cradle charging or a charging jack receptacle such as a standard cell phone charging jack receptacle. It should be understood that the computer instructions recorded in the computer accessible memory include an operating system for the mobile PERS unit. The computer-accessible memory may include programmable memory and/or non-programmable memory.

While various components are shown in FIG. 1 as separate and operably interconnected, it should be understood that various components may be provided and/or combined into one unit or integrated circuit. For example, a commercially available cell phone circuit module that contains a 3-axis accelerometer and a satellite positioning system may be used in the PERS device/pendant for fall detection and communication with the PERS call monitoring center. One suitable, commercially available module that provides various functions is the IEM6055 Internet of Everything Module (Qualcomm, San Diego, Calif., USA). The specifications and features of the IEM6055 include: Technology/Bands—Dual-Band 800/1900 MHz, CDMA2000 1X Voice/Data; Advanced RF Technologies—Standalone GPS, AGPS, gpsOneX-TRA™, Bluetooth 2.0 SW driver included; Data Speeds—CDMA 1xRTT FL/RL 153 kbps/153 kbps; Dimensions and Weight—21×22×4.4 mm, 4 grams; Interfaces—90-pin board-to-board connector including USB 2.0 Full Speed, Bluetooth 2.0 (UART1-data, AUX_PCM-audio), I2C, RUIM support, LCD (parallel or I2C), Camera (1.23MPixel), Keypad (5×5 matrix), Keypad backlight, 2 LED control lines, Vibrator control, General Purpose PDM (LCD backlight and brightness control), Audio—handset, headset, speaker, Primary antenna RF coax connector for both modem and GPS; Miscellaneous Features—On board accelerometer (Bosch, SMB380/BMA150, 3-axis), USB charging (Li-Ion), Output Interface voltages (1.8V, 2.6V, 2.85V); Module Software—AMSS6055, version TBD; APIs and SDKs—BREW Mobile Platform, AT command interface, Documentation; STANDARDS/CERTIFICATIONS—IS-2000 for CDMA 1xRTT, IS-707-A Data, IS-637-B SMS, IS-638-A Service provisioning, gpsOne™, IS-98 CDMA2000 Minimum Performance, Operator compliance, Infrastructure IOT compliance, FCC type acceptance, RoHS compliant, 1X Call<500 mA (23.5 dBm), GPS<50 mA (Standalone).

Thus, various functional units of PERS monitor/pendant embodiments of the invention may be provided by a single component or integrated circuit. Conversely, various components and functions of a monitor/pendant may be distributed among multiple components, modules or units.

Figure 2A:
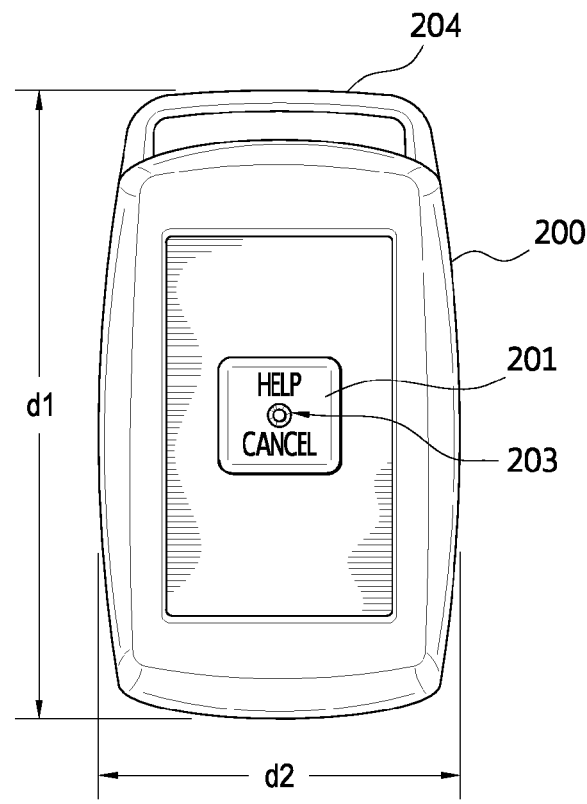
FIG. 2A shows the front side of a PERS pendant embodiment of the invention with a help/cancel button thereon.

FIG. 2A shows the front side of a PERS pendant embodiment of the invention. The apparatus has a housing 200 having an at least substantially rectilinear profile. Height d1 may be greater than width d2. The height may, for example, be up to 2.5 inches or at or about 2.5 inches and the width may for example be up to 1.5 inches or at or about 1.5 inches. The maximum thickness (front to back dimension) of the PERS pendant may for example, be up to 0.5 inches or at or about 0.5 inches. For simplicity and ease of use, a PERS monitor/pendant according to the invention as shown in FIG. 2A may have only one button 201 that can be used to manually trigger an alert and cancel an alert if desired. Such a device may also include at least one, such as one, light emitting element 203, such as light emitting diode (LED), as shown, to indicate battery status and/or for other indications as discussed herein. The light emitting element in the embodiment of FIG. 2A is disposed in the center of button 201 but may, for example, be disposed anywhere on the front of the pendant, or elsewhere on the housing. The pendant's housing also provides an extended eyelet structure 204 through which a lanyard (not shown) may be strung so that the device can be hung from a user's neck. In addition or alternatively, the pendant's housing may provide a recessed eyelet through which a lanyard may be strung so that the device can be hung from a user's neck or body.

Figure 2B:
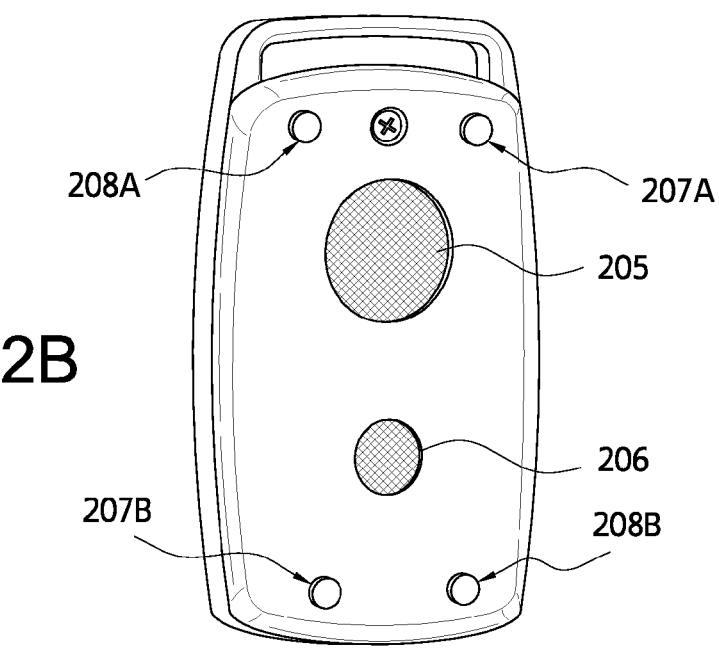
FIG. 2B shows the back of a PERS pendant embodiment of the invention with ECG electrodes and battery charging electrodes thereon.

FIG. 2B shows the back side of the PERS pendant embodiment of the invention shown in FIG. 2A. 205 and 206 are grills covering the speaker and microphone of the apparatus, respectively. Alternatively, both speaker and microphone may be disposed behind a single grill. With respect to its speaker phone function, the apparatus may be configured to operate in VOX (voice activated switch) mode such that only one party to a two party conversation can transmit audible communication at one time (when party A is speaking over party B's speaker, party B's microphone is inactivated). As shown, each of the pair of ECG electrodes 207A and 207B are disposed at or near diagonally related corners of the back side of the apparatus. This maximizes the distance between the ECG electrodes which increases the sensitivity and ECG signal strength obtainable with the apparatus. Two battery charging electrodes 208A and 208B are disposed at or near the two remaining, diagonally related corners. In addition, or alternatively, the battery charging contact electrodes could be disposed on another surface of the apparatus, such as on the bottom side of the apparatus (in the manner of a typical cordless telephone). In addition or alternatively, a charging jack configured to receive a charging plug, such as a standard cell phone charging jack and plug may be disposed in and presented by the apparatus. Thus, depending on the configuration, recharging the battery of the apparatus may include placing the apparatus into a charging cradle and/or inserting a charging jack into a charging jack receptacle of the apparatus. Still further, in addition or alternatively, the apparatus may include an induction charging circuit so that the battery may be charged by induction. The device may be configured so that the light emitting element, such as light emitting diode, flashes while the rechargeable battery of the apparatus is being charged and assumes a constant non-flashing on-state when the charging is complete.

Various features and functions of portable PERS apparatuses/pendants of the invention that may be used alone or in any combination are further described below with further reference to the appended figures.

Manual/Automatic Alerting

A manual alert is one in which the user presses the alert button on the apparatus/pendant to initiate an alert. Pressing the button on the pendant may also be used to cancel an alert after it has been initiated. Automatic alerting occurs when one or more on-board sensors, such as a tilt-switch and/or an accelerometer, detect changes in orientation and/or motion indicative of a fall. This process is performed by the at least one processor under control of the processor-implementable computer instructions stored in processor-accessible memory, based on inputs received from the sensor(s). The top level, monitoring mode and processing mode flow diagrams, FIGS. 3A, 3B and 3C, describe the logic sequences for these functionalities in one embodiment of the invention.

Figure 3A:
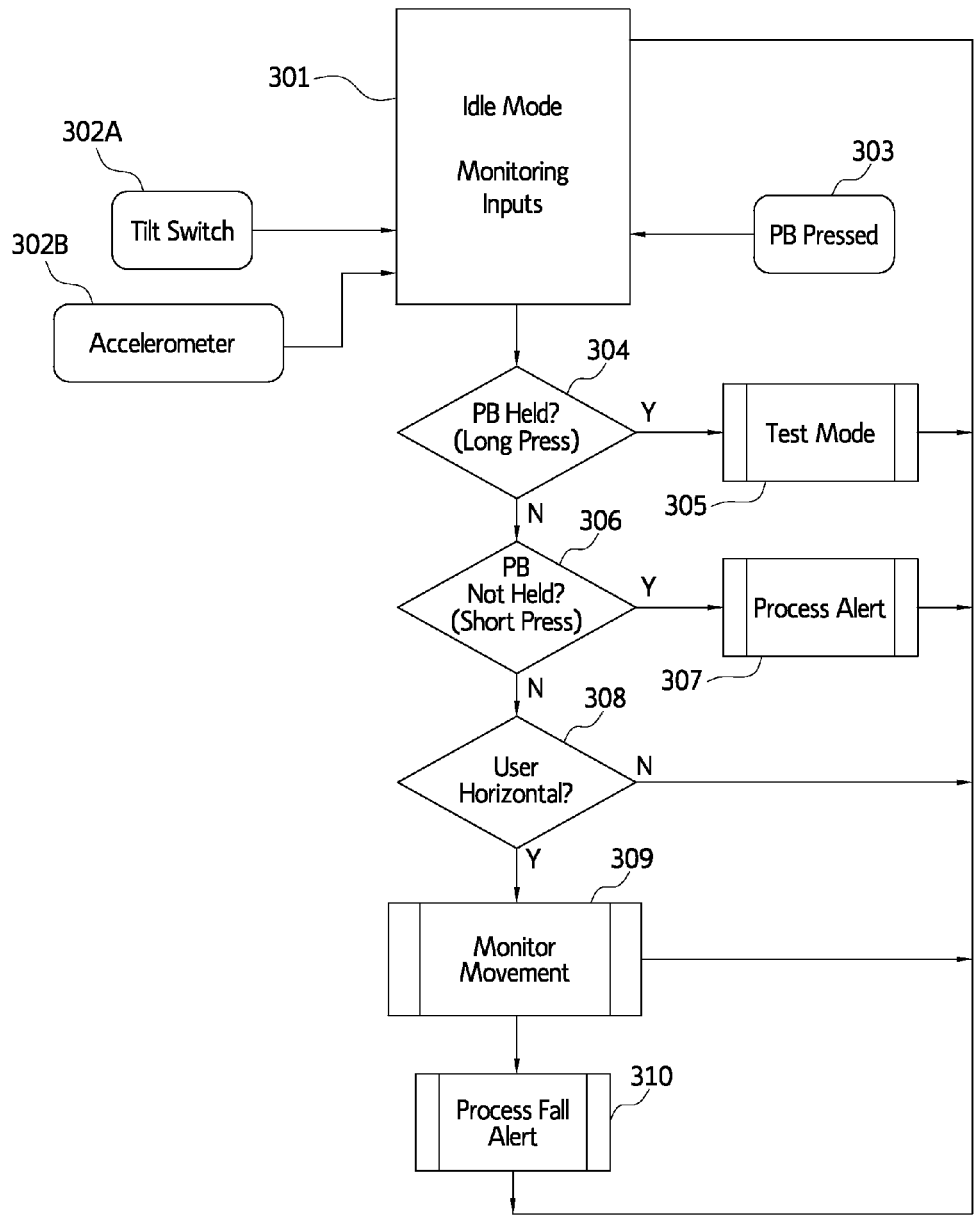
FIG. 3A is a top level flow diagram for a PERS pendant embodiment of the invention that includes a fall detection and alert function.

FIG. 3A is a top-level flow diagram illustrating the operations and process steps undertaken by one mobile PERS apparatus embodiment of the invention in connection with its manual alert and automatic fall detection alert functions. State 301 is the idle mode of the apparatus. In this state, the device is powered up, i.e., "on," and the processor under control of the computer instructions (operating system) monitors and is responsive to inputs that may be received from tilt switch 302A and/or accelerometer 302B indicating a change in the user's attitude and/or from press button (PB) 303. At 304, the device monitors if a push button press is a long press (above a preselected or preset threshold duration). If the press is a long press, the apparatus enters a diagnostic test mode 305. After the diagnostic test mode completes, the apparatus automatically returns to idle mode 301. If the press button has not been actuated by a long press, at 306 the apparatus checks if a short press was made (a press within a preselected or preset duration, shorter than the preselected or preset long press duration). If a short press has been detected, an emergency alert 307 is sent out by the apparatus to the call monitoring center (or call service center). After the emergency alert has been processed and any call between the user (the apparatus) and the call service center is complete, i.e., hung up, the apparatus returns to idle mode 301. If at 304 no long press is detected and at 306 no short press is detected, the apparatus checks the user's attitude, i.e., whether based on the state of the tilt switch the user is horizontal or vertical. If the user is not horizontal, the apparatus returns to idle mode 301. If at 308, it is detected/determined that the user is horizontal based on tilt switch 302A and/or accelerometer 302B, a horizontal movement monitoring process 309 is initiated. Process 309 monitors movement in the horizontal plane using input from a 3-axis accelerometer of the apparatus to detect if the user has voluntarily become horizontal, e.g. they laid down in bed, or whether they have fallen. Voluntary horizontal disposition is typically associated with horizontal motion, such as "shifting about" while involuntary horizontal disposition, resulting from a fall, is not. If this horizontal motion is detected, or if a manual cancel is requested at this point, the apparatus returns to idle mode 301. If this horizontal movement is not detected, it is indicative that the user is unconscious or incapacitated (e.g., paralyzed) and an emergency fall alert 310 is processed in which the apparatus calls the call service center.

Figure 3B:
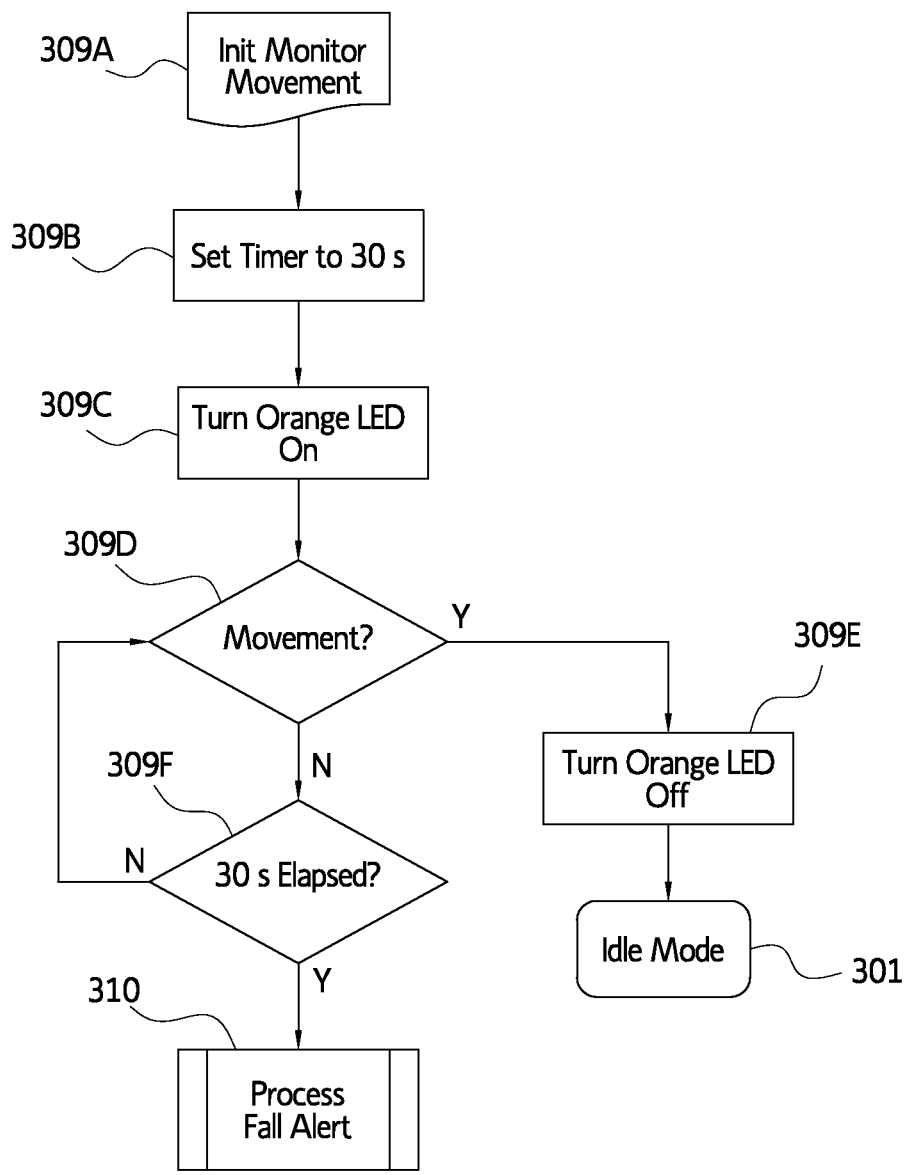
FIG. 3B is a movement monitoring flow diagram for a PERS pendant embodiment of the invention that includes a fall detection and alert function.

FIG. 3B is a flow diagram illustrating the horizontal movement monitoring process 309 of FIG. 3A in more detail. This process is intended to suppress false alarms such as in the case where the user voluntarily lays down in bed and fails to take off the pendant to place it in its recharging cradle. When the device detects that the user is horizontally disposed, the horizontal movement monitoring process 309A is initiated. At 309B, the apparatus begins a 30-second count and turns on an orange LED on the pendant 309C. At 309D, the device begins monitoring horizontal motion using output from its 3-axis accelerometer. If such horizontal motion is detected, it is indicative that the user is conscious and the apparatus responds by turning off the orange LED 309E and returning to idle mode 301. In the event horizontal motion is not already detected, the device continues to monitor whether the 30-second time period has elapsed (309F). If at 309F, the device detects that the 30-second time period has elapsed and no horizontal motion has been detected, it processes an automatic emergency fall alert 310, placing a call to the call service center and transmitting information relating to the alert thereto.

Figure 3C:
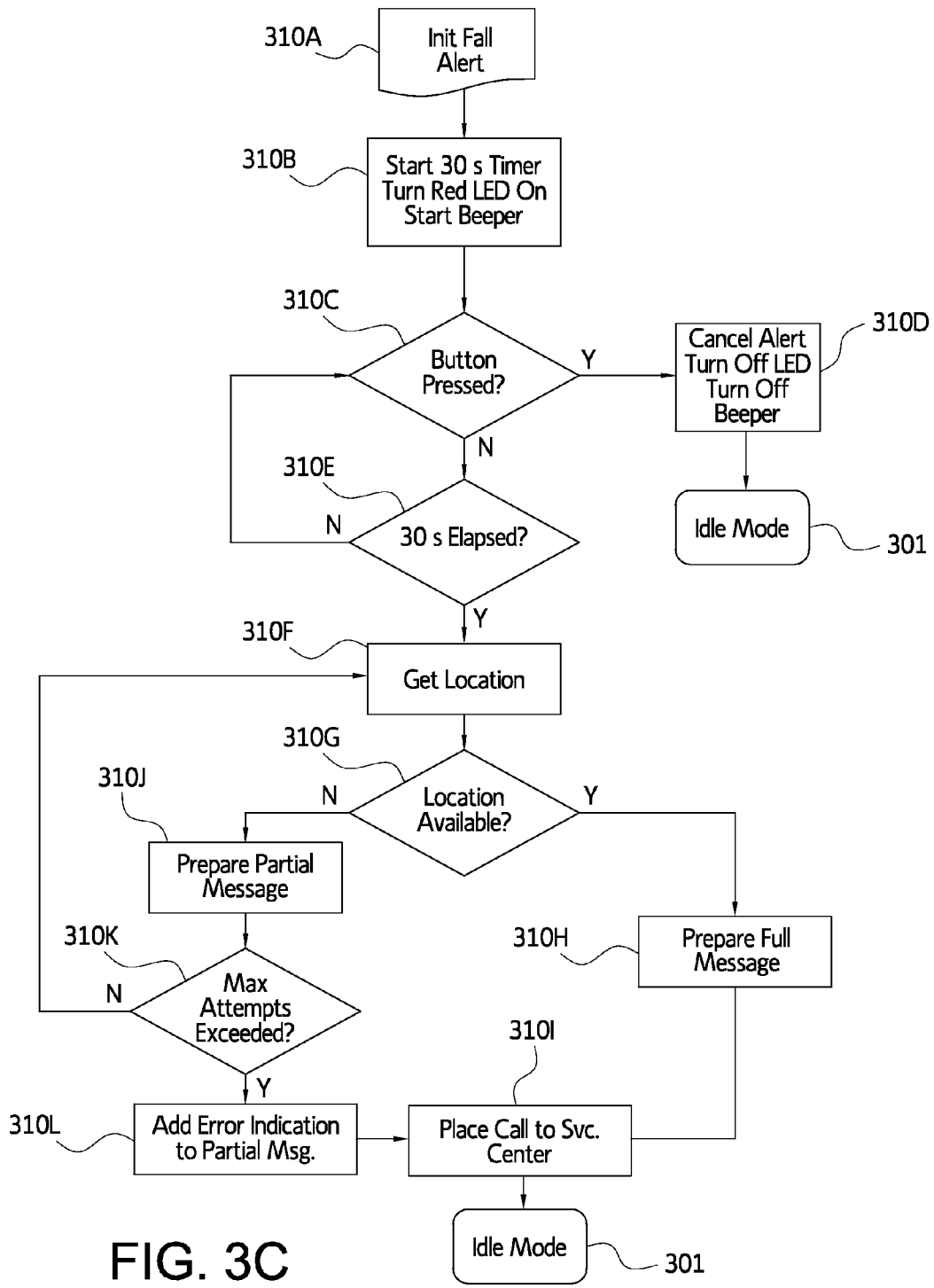
FIG. 3C is a fall alert processing flow diagram for a PERS pendant embodiment of the invention that includes a fall detection and alert function.

FIG. 3C is a flow diagram illustrating the process fall alert segment 301 of the embodiment of FIG. 3A in more detail. At 310A, the fall alert process is initiated and at 310B a 30-second timer is begun, a red indicator LED is turned on and the mobile PERS apparatus provides an audible alarm such as beeping to the user. At step 310C, the apparatus monitors whether the push button has been pressed to cancel the otherwise forthcoming emergency call by the apparatus to the call service center. If the button is pressed, the fall alert process is canceled, the red LED and audible alarm are turned off (310D) and the apparatus returns to idle mode (301). If the button has not been pressed, the apparatus continues to monitor whether the button is pressed during the 30-second period (310C). If the 30-second period elapses without detecting that the button has been pressed, the apparatus attempts to obtain its geographic location using, for example, an integral A-GPS module (310F). If the location can be obtained (310G), the apparatus prepares an emergency alert data message that includes the location information (310H) and transmits it in a call to the call service center (310I). A voice connection is also made between the apparatus and the call service center. When the call is hung up, the apparatus returns to idle mode 301. If the apparatus attempts to obtain the user's (apparatus') location at 310G but is not able to, the apparatus prepares a partial emergency alert data message without the location information for transmittal to the call service center (310J) but continues to attempt to obtain the geographic location until success or a number of maximum attempts has occurred (310K). If the number of maximum attempts to obtain the location is reached without success, the partial message without the geographic location information but with an error code (indicating that the location was unobtainable) is prepared (310L) and transmitted in a call to the call service center (310I). A voice connection is opened as previously described. When the call is hung up, the apparatus returns to idle mode 301.

Intelligent Fall Detection

Figure 4:
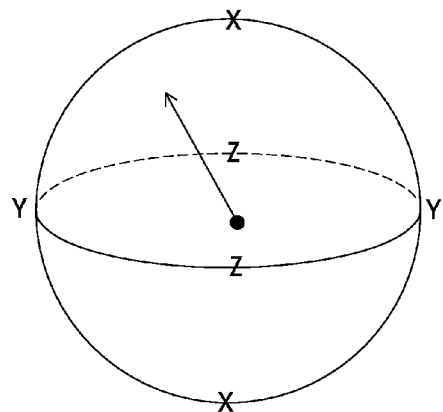
FIG. 4 shows a spherical reference model that may be employed in connection with PERS embodiments of the invention that include a fall detection function.
Figure 5:
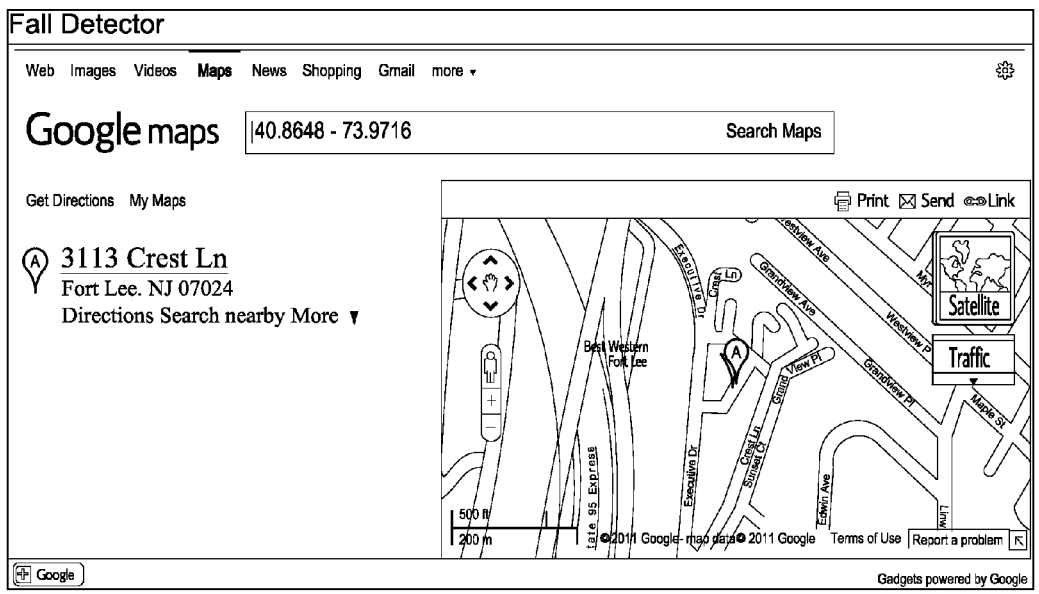
FIG. 5 illustrates how GPS coordinates received from a PERS apparatus embodiment of the invention may be used to query a locational search engine to identify a street address.

The algorithm for intelligent, automatic fall detection may, for example, use the voltage output from the 3-axis accelerometer as follows. The three axes are defined as X, Y and Z as shown in FIG. 4. The X-axis represents standing or sitting upright, Y-axis for lying on one's side (left or right side) and Z-axis for lying on one's stomach or back. The accelerometer, in addition to measuring acceleration or deceleration, monitors position and the X, Y and Z voltage outputs are in direct proportion to the gravitational pull of the earth. Therefore, when standing or sitting the output for X>Y and X>Z; when lying on one's side, Y>X and Y>Z and; when on ones back or stomach, Z>X and Z>Y. For practical purposes it is assumed that when standing or sitting, where X>Y and X>Z, that this is not a fall and is defined as the Standard Position. For example, if a user were to fall and land on one's side, the output of the accelerometer would go from the Standard Position to Y>X and Y>Z indicating a fall. This starts a 30-second timer allowing the user to temporarily change positions and return to the Standard Position or the non-fall position. If the user remains on his/her side for more than 30 seconds (fall evaluation period) without any movement, an alert is automatically initiated to the service center. If the user has intentionally gone from the Standard Position to a different position and motion is detected during the 30-second fall evaluation period, no alert is initiated. If the user later returns to the X-position, the algorithm is reset. A more complex algorithm for intelligent fall detection can be also be compared to a spherical reference (FIG. 4) and uses X (as being upright) and not a fall condition, Y (as being on the user's side) considered a fall condition, and Z (as being on the user's back or stomach) also considered a fall condition. The spherical reference model of FIG. 4 showing X>Y and X>Z depicts a Standard Position condition (upright, and not a fall). If it is assumed that the output of X, Y and Z can range from 0 to 1, then if X<1 but >Y, and X<1 but >Z, then the wearer (user) is at an angle that is considered as not being a fall. Here again, the 3-axis accelerometer may be used to determine or infer body position. When standing or sitting in an upright position and perpendicular to the earth, the voltage output from X (±a tolerance) is greater than the output from Y (±a tolerance) and also greater than the output from Z (±a tolerance). In one embodiment, a PERS apparatus of the invention that is equipped with a 3-axis accelerometer is provided with software embodying standard or custom learning algorithms such as those known in the art so that the apparatus via its processor under control of said software can learn what angle or angles are normal for that particular user and monitor the user for deviations accordingly.

The PERS pendants/apparatuses of the invention may, in addition or alternatively, employ and embody other fall detection methods and systems such as but not limited to any of those disclosed in co-owned U.S. Pat. No. 6,819,247, which is hereby incorporated by reference in its entirety.

Mobility Outside of the Home with Address and/or Geographic Location Determination In order to provide emergency alert coverage to a user who is not present at home, a PERS apparatus of the invention may incorporate a locational positioning system such as GPS (Global Positioning System) or A-GPS (Assisted Global Positioning System), so that it may determine its precise location and transmit the user's position to the call service center upon an alert. The A-GPS system/module used may be the same type of GPS system found in smart cell phones in which the cell phone tower assists the GPS and eliminates the requirement for direct line of sight with the GPS satellite system. More generally, the apparatus may include a terrestrial positioning system/module, a satellite positioning system/module, or combinations thereof. Satellite-based geographic coordinate finding and locating systems that are suitable for use according to the invention include, for example, the Global Positioning System (GPS), the European Galileo system and the GLONASS system. Terrestrial positioning systems suitable for use according to the invention include, for example, Enhanced Observed Time Difference (E-OTD), Time Difference of Arrival (TDOA), Angle of Arrival (AOA).

PERS apparatus embodiments having an integrated positioning module may also be used to generally track the user, e.g., at particular times or at regular intervals such as but not limited to every 20 minutes or every hour, for safety purposes, such as to safeguard against wandering for users deemed to be at risk for such behavior, to detect unusual periods of immobility in or outside the home, or to simply ensure that the user has safely returned to their abode by an expected hour. In response to deviations from normal, usual and/or expected activity, a voice call may be placed to a user by the call service center to the user's apparatus and/or to third-party contacts in order to check the status of the user. If the user indicates they require assistance or if the user is non-responsive to the call placed to the PERS apparatus, the call service center may escalate their response by contacting third-party contacts and/or by dispatching emergency personnel to the user's location. PERS apparatuses of the invention that include a speaker phone module may be configured such that the user does not need to pick-up (or accept) an incoming call from the call service center. Instead, the PERS apparatus may be configured to automatically pick-up calls from the call service center so that the speaker of the apparatus can immediately provide audible communications to the user without requiring any action by the user.

Two-Way Voice and Data Communication

PERS apparatus embodiments of the invention may incorporate an integral cellular telephone module with speakerphone function that allows the call service center and user (if conscious), or third-party present at user's location, to talk to each other, for example, in order for the user/third-party to describe the situation and type of assistance required and to receive any instructions from the call service center. In addition, the cell phone module may be configured to send a text message (SMS) to another predetermined/preselected cell phone number (such as of the call service center and/or of a family member and/or of the user's doctor) and/or to a predetermined email address, for example with a link to the geographic location and/or address of the user and/or contact information for the service center when an alert occurs. FIG.

5 shows how GPS coordinates data received from a portable PERS apparatus can be entered into a locational search engine, such as Google Maps®, to retrieve corresponding street address information. Data for an ECG (electrocardiographic) rhythm strip, if taken, can be transmitted as well from the PERS device to the call service center and/or other preselected and preprogrammed destinations (such as to the user's doctor).

ECG (Electrocardiographic Rhythm Strip)

PERS apparatus embodiments of the invention may include an ECG monitoring circuit such as that shown in FIG. 6 that is used to monitor the user's ECG and performs an A/D conversion of the analog signal at a frequency of 500 to 2,000 Hz (or 0.5 to 2 msec). FIGS. 7A and 7B show sample digitized output of an electrocardiographic monitoring circuit that may be used in a PERS device embodiment of the invention with normal reference (baseline) data (FIG. 7A, shown above) and abnormal (elevated T wave, increased beats per minute (BPM)) data (FIG. 7B, shown below). Both the initial baseline data and the emergency test data (or later generated test data generally) may be obtained using the ECG electrodes of the wearable pendant. The user can, for example, place the pendant against his/her chest or place a right finger and a left finger, each to one of the two electrodes, to begin the electrocardiographic recording. A caretaker or other third-party may also press the electrodes to the user's chest to obtain the ECG rhythm strip data. The PERS pendant may be configured to automatically take the ECG data upon the ECG electrodes being placed against the user's body (typically to his/her chest or held to fingers of opposite hands). The pendant may be configured such that the ECG circuit is inactive when there is high impedance between the two ECG electrodes as when there is only air separating them, but is activated upon the drop of impedance experienced when the electrodes are contacted with the user's body. The device may be configured to wait for a preselected duration of time, for example, 5 or 10 seconds, in which the drop in impedance is uninterrupted before it automatically begins recording electrocardiographic data. In this manner, the device ensures that good contact has been made between the user's body and the ECG electrodes before recording is begun.

In one aspect of the invention, reference or "baseline" electrocardiographic readings/information is obtained from a person who is/will be the user of the ECG-enabled mobile PERS apparatus and is stored for later retrieval in computer-accessible memory so that it can be compared to electrocardiographic readings/information taken later from the user (e.g., during a potential emergency or cardiac event situation or simply as a check-up) using his/her ECG-enabled PERS apparatus. The reference/baseline electrocardiographic readings/information (such as ECG rhythm strip data) may be stored in the computer-accessible (processor-accessible) memory of the PERS apparatus and/or in remote computer-accessible memory accessible to a computer system of the call service center such as in a data structure, for example, in a relational database, wherein it is correlated to personally identifiable information for the user such as the user's name and/or identification number, etc. In the case the reference/baseline electrocardiographic readings/information is stored in the computer accessible memory of the PERS apparatus, the apparatus may configured (via hardware and/or software computer instructions) to transmit that data to the call service center, at least when later test electrocardiographic readings are taken for the user using the apparatus and transmitted to the call center. In the case the reference/baseline electrocardiographic reading/information is stored in the computer-accessible memory of the PERS apparatus, the apparatus may alternatively be configured to transmit the reference/baseline electrocardiographic data to the call service center whenever any alert is activated, such as a manual alert or an automatic fall alert. Further, it should be understood that in the case the reference/baseline electrocardiographic reading/information is stored in the computer/processor-accessible memory of the PERS apparatus as referred to herein, what is meant is that said data is persistently stored, for example, for at least one or more days, one or more weeks or one or more months, and not just momentarily stored.

A reference/baseline electrocardiographic reading may be taken using the ECG electrodes of the apparatus by the user himself/herself and/or with the assistance of a caretaker or medical personnel such as a doctor or nurse. In one embodiment, the apparatus' ECG recording function is automatically activated when the ECG electrodes are contacted with the user's skin, for example, on his/her chest or by holding a finger of each hand to the ECG electrodes. The reference/baseline data so-obtained may be stored in the memory of the apparatus and/or transmitted to a remote computer-accessible memory, for example of a call service center computer system. In another embodiment, the manual alert button on the ECG-enabled PERS apparatus is pressed to initiate a call with the call service center or a call is made by the call service center to the apparatus. The call center attendant (live or automated) is instructed to prepare to receive a reference/baseline ECG reading and/or tells the user to proceed with the reading by contacting the ECG electrodes of the apparatus to himself/herself for a period of time.

The duration of electrocardiographic recording may, for example, be at least 10 seconds, such as in the range of 10-300 seconds or in the range of 20-300 seconds. The PERS apparatus may be provided with nonvolatile memory such EEPROM or Flash (for example, Frequency Response: 0.5 to 30 Hz CMRR: 70 dB (min.) Input Dynamic Range: ±2.5 mV Resolution: 8 bits, 100 s/s) to store the electrocardiographic data.

The ECG-enabled PERS apparatus may, for example, also be configured for and used to take multiple follow-up ECG recordings, for example, once a week, according to doctor's instructions or as requested by medical personnel. In this manner, the apparatus can be used to regularly monitor a user's cardiac function even in the absence of a putative emergency situation. Data from these regular readings may be stored in the memory of the PERS apparatus and/or transmitted for remote memory storage to the call service center's computer system and/or third-parties such as the user's doctor.

Figure 8:
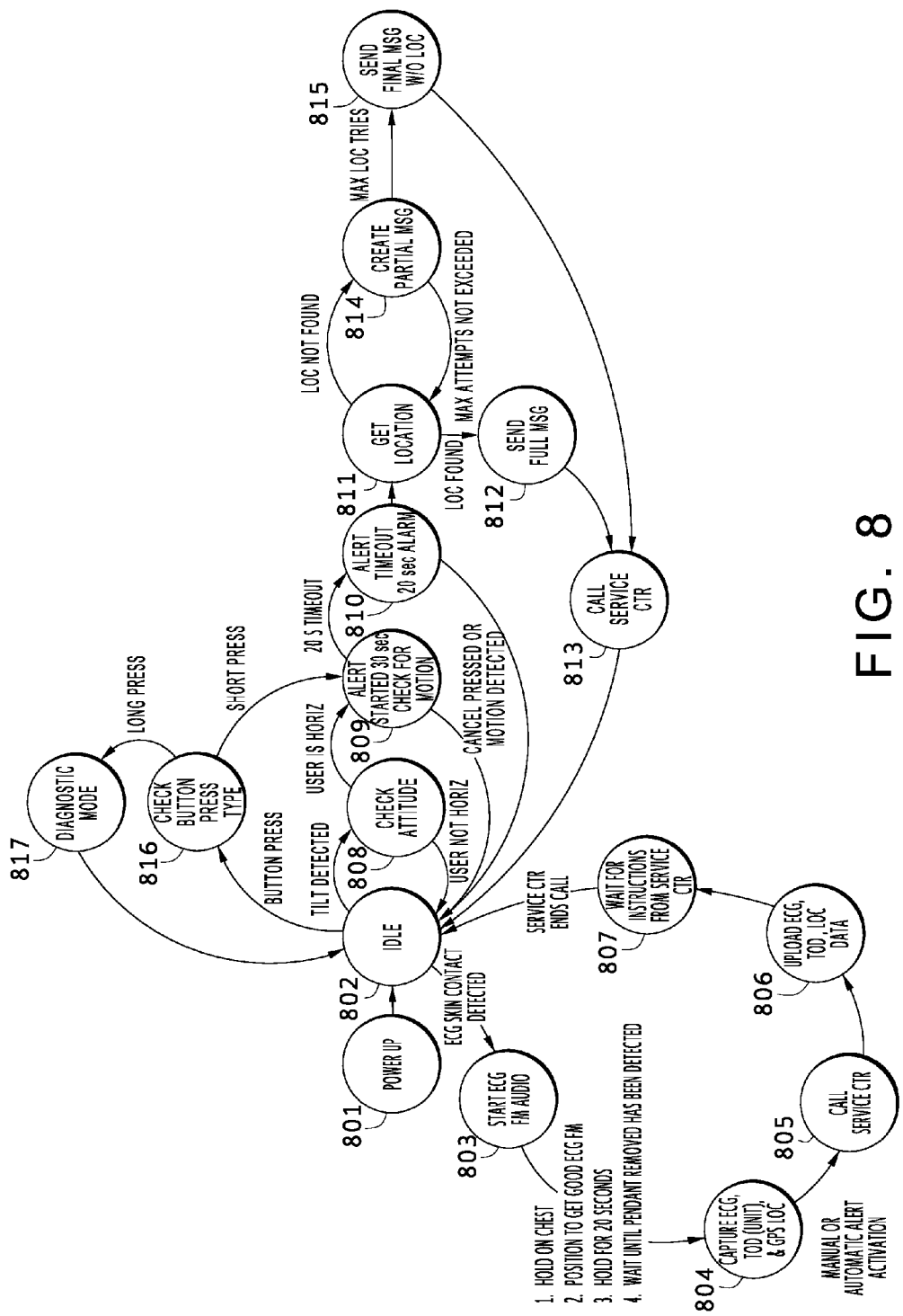
FIG. 8 is a state diagram for a PERS apparatus embodiment of the invention.

FIG. 8 is a state diagram for a mobile PERS apparatus embodiment of the invention showing the various states and functions of the apparatus and its subsystems and steps in their operation. From an off state, the apparatus is turned on (powered up) 801 and enters its idle mode 802. States 803 to 807 relate to the ECG functions of the apparatus. When a decrease in impedance between the ECG electrodes is detected when the electrodes are placed against the user's skin, the apparatus begins to output frequency modulated (FM) audio of the ECG signal. A user will typically be trained to recognize what the audio output should sound like when good ECG electrode contact is made with the skin. The user will, for example, hold the ECG electrodes of the PERS apparatus to his/her chest and position the apparatus (or hold a finger on one hand to one ECG electrode and a finger of the other hand to the other ECG electrode) until a constant ECG audible signal is heard, and hold that position for a recommended period of time such as at least 20 seconds, for example 20 seconds, during which the apparatus records the ECG data in processor/computer-accessible memory. The apparatus detects when contact is broken between the ECG electrodes and the user's skin by sensing the increase in impedance between the electrodes. At state/step 804, the apparatus captures the time of day (TOD) and date and GPS location of the ECG recording and stores the ECG data, time and date and GPS location in the computer-accessible memory. In response to a manual alert initiated by a user pressing the press button of the apparatus, or in response to an automatic alert, or in response to taking an ECG reading with the apparatus, in step 805 the apparatus calls the call service center using the integrated cell phone module (or other wireless communications module) and transmits 806 the recorded ECG, time and date and location data to the call service center. Time and date may for example be determined, for example, using an integral electronic clock and calendar of the PERS apparatus or by any means. At 807, the apparatus keeps the call open for voice communication between the service center and the user. The device is preferably configured so that only the service center personnel, and not the pendant user, are able to hang up the call. Upon the call being hung up by the call service center, the apparatus returns to idle mode 802. The unique cellular telephone number of the PERS apparatus may act as the identification code for the unit and its user. The call service center may maintain a computer system that in response to receiving a call from a particular apparatus telephone number, uses the number to automatically retrieve the user's information such as but not limited to the user's name, address, the family and medical contact information, from a computer-accessible relational database and presents such information to the service center personnel on an output device such as a display. The computer system of the call service center may also be configured to store in computer-accessible memory data received from a user's PERS apparatus, such as baseline and/or any follow-up electrocardiographic data obtained from the user using his/her PERS apparatus.

States/steps 808-815 relate to the automatic fall detection feature of the apparatus of the embodiment of FIG. 8. If the apparatus detects a tilt, i.e., that the user's attitude is at least partially horizontal (e.g., beyond a preset threshold or totally), using the output of its integrated tilt switch and/or 3-axis accelerometer, it begins monitoring the user's orientation 808, checking to see if the user has returned, for example, within 2-3 seconds, to a vertical position. If the user has returned to a vertical position within the preselected time period, such as 30 seconds, the apparatus returns to idle mode. Thus, if a user has bent over to retrieve an item from the floor but returns quickly to an upright position, the apparatus interprets that this is not a fall situation and returns to idle mode. On the other hand, if the apparatus detects that the user has not returned to an upright position, i.e., the user remains horizontal, for the preselected threshold duration, at 809 the apparatus provides an audible signal such as a beep and/or voice instruction to indicate that that the transmission of an alert to the call service center will be forthcoming unless the button is pressed to cancel the call. In addition, during this state (809), the apparatus uses the 3-axis accelerometer to determine if body motion indicative of voluntary horizontal disposition (laying down) is present, in contrast to relative lack of motion in the horizontal plane that is typically associated with a fall condition. If the former is detected, the alert is automatically cancelled. If after a preselected length of time, such as 20 seconds, horizontal plane motion indicative of voluntary horizontal disposition is not detected (810), the apparatus begins an alert process shown in states/steps 811-815.

In state/step 810, the apparatus provides an audible alarm to the user for 20 seconds to indicate that an emergency alert is about to be sent to the call service center. If the user does not cancel during this 20-second period, the apparatus attempts to obtain its GPS location 811. If the location is obtained, the apparatus sends an emergency alert message to the call service center 812 containing, for example, the GPS location and accelerometer data recorded during the incident. In state/step 813, a voice call between the apparatus and call service center is established in which the service center personnel may attempt to communicate with the user. Emergency personnel may be dispatched to the user's (apparatus') location during this time. The call remains open until the call service center hangs up, at which point the apparatus is returned to idle mode 802.

If in state/step 811, the apparatus is not able to obtain the GPS location, a partial emergency message (without the GPS location data) is created 814 but the apparatus continues attempting to obtain the GPS location for a preselected maximum number of times. If the GPS location is determined, a full emergency message (including GPS coordinates) is sent in step 812 as described before. If the GPS location cannot be determined within the preset maximum number of tries, a final emergency message without the GPS location information 815 is sent to the call service center. A voice call between the apparatus and the call service center 813 is opened concomitantly with step 815 during which the call center personnel may attempt to communicate with the user. The apparatus may optionally be further configured (not shown) to continue attempts to obtain and transmit GPS location information after having sent the partial emergency alert message without GPS data at 815.

The apparatus may be configured so that the light element, which may be a light emitting diode (LED), such as a multi-color LED, and the audible alarm, such as a beeping alarm, operate in the following manner. In idle mode, the light is off and the audible alarm is off. When a putative alert is begun 809, the light element is turned on in a first color such as red but the audible alarm is off. If the alert is not automatically or manually cancelled during a 30-second period in 809, the apparatus proceeds to state 810 in which the light is on in the first color (red) and the audible alarm, such as a beeping, is on. This serves as a final warning to a user that an emergency alert call to the call service center will be placed in 20 seconds. For example, if a user lays down voluntarily but is not in an emergency situation, the alarm will alert the user to cancel what would be a forthcoming false alarm. If an emergency response call is successfully made by the apparatus, the light may illuminate in a second color such as green, for example, for five seconds. If an alert is cancelled, the light may also illuminate in a different color, such as blue, for example, for five seconds. Such PERS apparatuses may employ a commercially available RGB tricolor LED.

It should be understood however, that the invention also provides related embodiments in which on an individual apparatus basis or system-wide (among a plurality of PERS apparatuses), the PERS apparatuses are configured or configurable so that an alert may not be canceled by the user pressing the button of the apparatus, but that only call center personnel may "cancel" the alert following its initiation, i.e., cancel dispatch of emergency personnel to the user, after speaking with the user via the integrated cellular telephone.

Steps/states 816 and 817 relate to user-initiated actuation of the press button of the apparatus. The apparatus is configured to monitor whether the button is pressed 816 and the duration of the action. A short press of the button, i.e., within a preselected duration, causes the apparatus to enter state 809 and the apparatus of the device proceeds as previously described from that point. A long press of the button i.e., beyond the short-press preselected duration, causes the apparatus to enter a diagnostic mode, after which the apparatus returns to idle mode 802. In addition to or as an alternative to the long button press activation of diagnostic mode (816 and 817), the apparatus may be configured to automatically enter the diagnostic mode when it is placed in the recharging cradle (or otherwise connected to a recharging apparatus). The apparatus may be configured such that in response to a long press of the button and/or upon being placed in the recharging cradle (or otherwise connected to a recharging apparatus) it receives and installs any software updates that may be available as well as transmits performance information such as that regarding battery performance.

Without limitation, the invention also provides the following embodiments.

One embodiment of the invention provides a personal emergency response system apparatus that includes:

a portable housing sized and configured to be hand carried, held in pocket (i.e., pocket-sized), and/or removably attached to a human user or clothing worn by the user;

at least one processor;

processor-accessible memory;

processor-implementable computer instructions stored in the processor-accessible memory;

a wireless transmitter or transceiver, such as a cellular telephone transmitter or transceiver, module operably linked to the processor;

an electrocardiographic monitoring circuit operably linked to the processor;

at least two, such as two, electrocardiographic monitoring electrodes operably connected to the electrocardiographic monitoring circuit, said electrodes being at least partially externally disposed for contact with the user's body; and a user input device such as a manual input device, such as a manual alert button (e.g., press button) or switch (e.g., a toggle switch), operably linked to the processor;

said computer instructions configured to direct the at least one processor to perform the steps of:

transmitting electrocardiographic data obtained from the user using the apparatus to at least one remote recipient using the wireless transmitter or transceiver, and in response to actuation of the user input device, transmitting an emergency alert message to a to at least one remote recipient using the wireless transmitter or transceiver module. The at least one processor, the processor-accessible memory, the wireless transmitter or transceiver and the electrocardiographic monitoring unit may be disposed within the housing. The computer instructions may be further configured to perform the step of: storing the electrocardiographic data obtained from a user using the apparatus in the processor-accessible memory of the apparatus, for example, before the step of transmitting the obtained electrocardiographic data.

The apparatus may be configured to automatically initiate electrocardiographic data recording in response to a drop in impedance between the ECG electrodes when said electrodes are contacted with the user's body. The apparatus may be configured to automatically initiate electrocardiographic data recording in response to a drop in impedance between the ECG electrodes when said electrodes are contacted with the user's body but only after the drop in impedance is sustained for a preset duration, for example, 5 seconds. This ensures that the user has made good contact with the ECG electrodes and prevents accidental recording if the ECG electrodes make brief incidental contact with the user's body.

The apparatus may be configured to audibly indicate for example, by tones and/or verbal messages, to the user when proper contact with the user's skin to detect an ECG signal is made. The apparatus may be configured to audibly indicate, for example, by tones and/or verbal messages, to the user when the ECG recording has been completed.

The apparatus may include a cellular telephone transceiver and a microphone and a speaker, each operably linked to the cellular telephone transceiver. The apparatus may be configured for audible two-way communication via the cellular telephone transceiver. The apparatus may be configured so that the at least one processor is operably linked to the microphone to provide audible indications to a user. The apparatus may lack telephone dialing buttons, i.e., lack the numeric or alpha-numeric keypad that is typically associated with a telephone. The apparatus may be configured such that the user is not able to input a telephone number of his/her choice into the apparatus to initiate a telephone call to the number but can only initiate a call to the call service center.

The apparatus may include a geographic location detection device capable of detecting the geographic location of the apparatus, said geographic location detection device operably linked to the processor. In this case, the computer instructions may be further configured to direct the at least one processor to perform the step of: in response to actuation of the manual alert button, transmitting the geographic location of the apparatus as determined by the geographic location detection device to at least one preselected remote recipient, for example, a remote recipient associated with a preselected telephone number such as that of the call service center or 911, using the wireless transmitter or transceiver. The geographic location detection device may be a GPS or A-GPS module. In this case, the geographic location information transmitted may include the GPS coordinates of the determined location.

The apparatus may further include fall detection means. For example, the apparatus may include one or both of a tilt-switch and an accelerometer, such as a 3-axis accelerometer, operably linked to the at least one processor. In this case, the computer instructions may be further configured to direct the at least one processor to perform the step of: in response to the detection by the tilt-switch and/or accelerometer of a change in orientation and/or acceleration, transmitting an emergency alert message to at least one remote recipient using the wireless transmitter or transceiver module. If the apparatus also includes the geographic location determining device as described above, the computer instructions may be configured such that a determination of geographic location is made in response to said change in orientation and/or acceleration that triggers an emergency alert message and the emergency alert message transmitted to the least one remote recipient using the wireless transmitter or transceiver includes the location information.

The apparatus and computer instructions stored in the processor-accessible memory thereof may further be configured to provide for the user to cancel an alert, such as a manually initiated alert and/or or an automatic alert (triggered by change in orientation or motion), for example, by pressing the user button of the apparatus, such as once or for a set number of times, after an alert has been initiated.

The PERS apparatus may include a rechargeable battery to power the device. The rechargeable battery may be disposed within the housing. The housing may, for example, have an at least substantially rectilinear profile (viewed from front or back), a front side, a back side and sidewall sides therebetween. The apparatus may include at least two, such as two, ECG electrodes disposed on the same side of the apparatus.

For example, at least two, such as two, ECG electrodes may be at least partially exteriorly disposed on the front side or on the back side of the housing, for example, at or near diagonally related corners of the front side or back side of the housing, or on a sidewall side of the apparatus housing.

A related embodiment of the invention provides a multi-user personal emergency response system that includes:

a plurality of personal emergency response system apparatuses capable of and configured for electrocardiographic data recording, for example, according to any of the embodiments or variations thereof described herein, each assigned to an individual user; and a call monitoring center computer system comprising:

at least one processor, processor-accessible memory operably linked to the at least one processor, processor-implementable computer instructions stored in the processor-accessible memory, at least one communications module capable of receiving data, such as digital data and/or voice data, transmitted by the plurality of personal emergency response systems apparatuses; and at least one display operably linked to the at least one processor, said computer instructions configured to direct the at least one processor to perform the step of:

storing electrocardiographic data received by the central monitoring system from a personal emergency response systems apparatus of a user in the computer-accessible memory of the call monitoring center computer system, wherein said data is correlated to the user therein. The system's communication module(s) may also be configured to transmit data such as digital data and/or voice data to the users' PERS apparatuses. The personal emergency response system apparatuses may be configured, for example by way of integral cellular telephone transmitters or transceivers to communicate with a remote recipient such as the call monitoring center (call service center) without the need for, or use, of a home (tethered) base station for each user or for any user. Thus, a multi-user system as described may lack such base stations. However, it should be understood that the invention also provides corresponding embodiments of PERS apparatuses/pendants, systems and methods in which the apparatuses are configured to communicate with a call monitoring center via a tethered base station, such as one connected to a conventional telephone line (land-line), and in such cases the corresponding multi-user systems may include such base stations for one or more of the users.

Another embodiment of the invention provides a method for obtaining an electrocardiographic reading from a human user using an ECG-enabled portable/wearable personal emergency response system apparatus that includes the steps of:

obtaining reference (baseline) electrocardiographic data from a user of an ECG-enabled personal emergency response apparatus such as a portable personal emergency response apparatus according to any of the embodiments or variations described herein, wherein the reference (baseline) electrocardiographic data is obtained by contacting the ECG electrodes of the apparatus with the user's body, for example, under non-emergency conditions; and storing or causing the storage of the reference (baseline) electrocardiographic data in a computer-accessible memory. The step of storing or causing the storage of the reference (baseline) electrocardiographic data in a computer-accessible memory may include storing or causing the storage of said data in the computer-accessible memory of the PERS apparatus itself and/or in a remote computer-accessible memory where it is accessible to the computer system(s) of the call service/monitoring center so it can be retrieved to be examined by call center personnel.

For example, the data may be stored remotely in a computer-accessible tangible memory storage medium in a data structure such as a database, for example a relational database, such as but not limited to a SQL database so that is later retrievable by a call service center that monitors incoming alerts of users of apparatuses according to the invention. The electrocardiographic reference (baseline) data for a user may be stored remotely in a data structure in which it is correlated to personally identifying information of the user such as but not limited to their name and address, an identification code such as the cellular telephone number of a PERS apparatus having a cellular telephone module, and/or other relevant information such as the names and contact information designated as emergency contacts for the user and/or medical information of the user that can be provided to emergency response and medical personnel in the event of an emergency.

Another embodiment of the invention provides a method for obtaining an electrocardiographic reading from a human user using an ECG-enabled portable/wearable personal emergency response system apparatus that includes the steps of:

as a user, obtaining one's reference (baseline) electrocardiographic data, by contacting the ECG electrodes of an ECG-enabled personal emergency response apparatus such as a portable personal emergency response apparatus according to any of the embodiments or variations described herein, with the one's body, for example, under non-emergency conditions to record electrocardiographic data, for example, electrocardiographic rhythm strip data, over a continuous period of time such as for at least 10 seconds, for at least 20 seconds, or in the range of 10-300 seconds or 20-300 seconds, wherein the obtained reference (baseline) electrocardiographic data is automatically stored in a computer accessible-memory such as in the computer-accessible memory of the PERS apparatus and/or in a remote computer-accessible memory where it is accessible to a computer system of the call service/monitoring center so it can be retrieved to be examined by call center personnel.

Another embodiment of the invention provides a method for managing electrocardiographic data of a human user obtained via an ECG-enabled portable/wearable personal emergency response apparatus that includes the steps of:

receiving in a data transmission from an ECG-enabled personal emergency response apparatus of a user, such as a portable personal emergency response apparatus according to any of the embodiments or variations described herein, reference (baseline) electrocardiographic data of the user, wherein the reference (baseline) electrocardiographic data was obtained by contacting the ECG electrodes of the apparatus with the user's body, for example, under non-emergency conditions; and storing the reference (baseline) electrocardiographic data in a computer-accessible memory, for example, remote from the apparatus. This embodiment may include the further step of providing an ECG-enabled portable personal emergency response apparatus according to any of the embodiments or variations described herein, for example, to the user, prior to the receiving step. The transmission may, for example, be sent wirelessly from the PERS apparatus to the recipient(s), for example via a cellular telephone network using an integrated cellular telephone transmitter or transceiver of the PERS apparatus. This embodiment may include the step of providing a call service/monitoring center computer system as described herein, which system receives and stores the baseline (reference) electrocardiographic data.

Another embodiment of the invention provides a method for managing electrocardiographic data of a human user obtained via an ECG-enabled portable/wearable personal emergency response apparatus that includes the steps of:

receiving in a data transmission from an ECG-enabled personal emergency response apparatus of a user such as a portable personal emergency response apparatus according to any of the embodiments or variations described herein personally identifying information (such as the telephone number of the apparatus or a user identification code) and test electrocardiographic data of the user, wherein the electrocardiographic data was obtained by contacting the ECG electrodes of the apparatus with the user's body, for example, in a putative emergency situation such as where the user has manually initiated an emergency alert and indicates to the call service center that he/she is experiencing shortness of breath, chest pains, dizziness, etc. or initiates an alert and transmission of ECG data by contacting the electrodes of the apparatus to their body; and storing the test electrocardiographic data in a computer-accessible memory, for example remote from the apparatus. This embodiment may include the further step of providing a portable personal emergency response apparatus according to any of the embodiments or variations described herein, for example, to the user, prior to the receiving step. In a variation of the embodiment, the data transmission may further include reference (baseline) electrocardiographic data of the user that was previously recorded from the user using the apparatus and stored in the computer-accessible memory of the apparatus. The storing step may still further include storing the received reference (baseline) electrocardiographic data of the user that was received from the user's PERS apparatus in computer-accessible memory remote from the user, e.g., in the computer system(s) of the call service/monitoring center. In a different variation, the embodiment includes the further step of: in response to receiving the data transmission/call, using the personally identifiable information of the data transmission to search for and/or retrieve reference (baseline) electrographic information of the user from computer-accessible memory remote from the apparatus, e.g., computer-accessible memory accessible to the computer systems of the call service/monitoring center. In this embodiment also, the transmission may, for example, be sent wirelessly from the PERS apparatus to the recipient(s), for example via a cellular telephone network using an integrated cellular telephone transmitter or transceiver of the PERS apparatus. In any of the embodiments and variations in which data stored in computer-accessible memory of a computer system of a remote call service center is retrieved, said data may be outputted on an output device such as a display and/or printer so that it may be viewed and/or acted upon by call service center personnel.

The aforementioned method embodiments may, for example, be performed within the environment of a system comprising multiple individual PERS apparatuses according to the invention that are assigned to different users, each of the apparatuses configured to communicate with a call service center that includes a call service center computer system, as described herein.

It should be understood that the term "user" as recited throughout this disclosure refers to a person, i.e., a human being. The user may be geriatric or non-geriatric. The user may have suffered an adverse cardiovascular event such as a heart attack or a stroke or be at risk of such an event. The user may have a cardiovascular condition, such as congestive heart disease, coronary artery disease (CAD), angina, hypertension or arrhythmia. The user may be a patient taking cardiovascular or cardiac medications such as one or more of anticoagulants, antiplatelet agents, angiotensin converting enzyme (ACE) inhibitors, angiotensin II receptor blockers (or inhibitors), beta blockers, calcium channel blockers, diuretics, vasodilators, digitalis preparations and cholesterol lowering agents such as statins.

Although the foregoing description is directed to the preferred embodiments of the invention, other variations and modifications may be made without departing from the spirit or scope of the invention. Moreover, features described in connection with one embodiment of the invention may be used in conjunction with other embodiments, even if not explicitly stated above.

What is claimed is:

1. A personal emergency response system apparatus, comprising:
   a portable housing sized and configured to be hand carried, held in pocket, or removably attached to a human user or clothing worn by the user;
   at least one processor;
   processor-accessible memory;
   processor-implementable computer instructions stored in the processor-accessible memory;
   a cellular telephone transmitter or cellular telephone transceiver operably linked to the processor;
   a speaker operably linked to the processor;
   an electrocardiographic monitoring circuit operably linked to the processor;
   electrocardiographic monitoring electrodes operably connected to the electrocardiographic monitoring circuit, said electrodes being at least partially externally disposed for contact with the user's body; and
   a user input device operably linked to the processor,
   wherein the at least one processor, the processor-accessible memory, the cellular telephone transmitter or transceiver and the electrocardiographic monitoring circuit are disposed within the housing,
   wherein said computer instructions are configured to direct the at least one processor to perform the steps of:
   transmitting the electrocardiographic data obtained from a user using the apparatus to at least one remote recipient using the cellular telephone transmitter or transceiver, and
   in response to operation of the user input device, transmitting an emergency alert message to at least one remote recipient using the cellular telephone transmitter or transceiver,
   wherein the apparatus is configured to automatically initiate electrocardiographic data recording in response to a drop in impedance between the ECG electrodes when said electrodes are contacted with the user's body, and
   wherein the apparatus is configured to audibly indicate to the user via the speaker when proper contact with the user's skin to detect an ECG signal is made.

2. The apparatus of claim 1, wherein the apparatus is configured to configured to audibly indicate to the user via the speaker when the ECG recording has been completed.

3. The apparatus of claim 1, wherein the apparatus is further configured to automatically initiate the electrocardiographic data recording after the drop in impedance is maintained without interruption for a preset duration.

4. The apparatus of claim 1, wherein the computer instructions are further configured to direct the at least one processor to perform the step of:
   storing electrocardiographic data obtained from a user by contacting the apparatus of the user with the user's body in the computer-accessible memory of the apparatus.

5. The apparatus of claim 1, further comprising a microphone and a speaker, each operably linked to the cellular telephone transmitter or transceiver module.

6. The apparatus of claim 1, further comprising a geographic location detection device capable of detecting the geographic location of the apparatus, said geographic location detection device operably linked to the processor, and
wherein the computer instructions are further configured to direct the at least one processor to perform the step of:
in response to actuation of the user input device, transmitting the geographic location of the apparatus as determined by the geographic location detection device to at least one remote recipient using the cellular telephone transmitter or transceiver.

7. The apparatus of claim 6, wherein the geographic location detection device comprises a GPS or A-GPS module.

8. The apparatus of claim 1, further comprising one or both of a tilt-switch and an accelerometer operably linked to the at least one processor, and
wherein the computer instructions are further configured to direct the at least one processor to perform the step of:
in response to the detection by one or more of the tilt-switch and the accelerometer of a change in one or more of orientation and acceleration, transmitting an emergency response message to at least one remote recipient using the cellular telephone transmitter or transceiver.

9. The apparatus of claim 1, further comprising:
a geographic location detection device capable of determining the geographic location of the apparatus, said geographic location detection device operably linked to the processor; and
one or both of a tilt-switch and an accelerometer, operably linked to the at least one processor, and
wherein the computer instructions are further configured to direct the at least one processor to perform the steps of:
in response to operation of the user input device, transmitting an emergency alert message comprising the geographic location of the apparatus as determined by the geographic location detection device to at least one remote recipient using the cellular telephone transmitter or transceiver, and
in response to the detection by one or more of the tilt-switch and the accelerometer of a change in one or more of orientation and acceleration, transmitting an emergency alert message, transmitting an emergency alert message comprising the geographic location of the apparatus as determined by the geographic location detection device to at least one remote recipient using the cellular telephone transmitter or transceiver.

10. The apparatus of claim 1, further configured to store baseline electrocardiographic information obtained using the apparatus in the computer accessible memory of the apparatus.

11. A multi-user personal emergency response system, comprising:
a plurality of personal emergency response system (PERS) apparatuses according to claim 1, each assigned to an individual user; and
a central monitoring computer system remote from the plurality of PERS apparatuses, comprising:
at least one processor,
processor-accessible memory operably linked to the at least one processor,
processor-implementable computer instructions recorded in the processor-accessible memory,
at least one communications module capable of receiving data transmitted by the plurality of personal emergency response systems apparatuses; and
at least one display operably linked to the at least one processor, wherein said computer instructions are configured to direct the at least one processor to perform the steps of:
storing electrocardiographic data received by the central monitoring system from a personal emergency response system apparatus of a user in the processor-accessible memory of the central monitoring computer system, wherein said data is correlated to the user therein.

12. A method for configuring a personal emergency response system device for electrocardiographic evaluation of a human user:
as a user, obtaining baseline electrocardiographic data from oneself by contacting the ECG electrodes of a personal emergency response system apparatus according to claim 1 with one's body under non-emergency conditions for a period of time,
wherein the obtained baseline electrocardiographic data is automatically stored in a processor-accessible memory for later retrieval.

13. The method of claim 12, wherein the period of time is at least 5 seconds.

14. The method of claim 12, wherein the processor-accessible memory is the processor-accessible memory of the personal emergency response system apparatus.

15. The method of claim 12, wherein the processor-accessible memory is processor-accessible memory of a remote computer system.

16. A personal emergency response system apparatus, comprising:
a portable housing sized and configured to be hand carried, held in pocket, or removably attached to a human user or clothing worn by the user;
at least one processor;
processor-accessible memory;
processor-implementable computer instructions stored in the processor-accessible memory;
a wireless transmitter or transceiver operably linked to the processor;
a speaker operably linked to the processor;
an electrocardiographic monitoring circuit operably linked to the processor;
electrocardiographic monitoring electrodes operably connected to the electrocardiographic monitoring circuit, said electrodes being at least partially externally disposed for contact with the user's body; and
a user input device operably linked to the processor,
wherein the at least one processor, the processor-accessible memory, the wireless transmitter or transceiver and the electrocardiographic monitoring circuit are disposed within the housing,
wherein said computer instructions are configured to direct the at least one processor to perform the steps of:
transmitting the electrocardiographic data obtained from a user using the apparatus to at least one remote recipient using the transmitter or transceiver,
in response to operation of the user input device, transmitting an emergency alert message to at least one remote recipient using the transmitter or transceiver,
wherein the apparatus is configured to automatically initiate electrocardiographic data recording in response to a drop in impedance between the ECG electrodes when said electrodes are contacted with the user's body, and wherein the apparatus is configured to audibly indicate to the user via the speaker when proper contact with the user's skin to detect an ECG signal is made.

17. The apparatus of claim 16, wherein the wireless transmitter or transceiver is configured to transmit the electrocardiographic data and the emergency alert message via a communications base station at the user's residence.

18. The apparatus of claim 17, wherein the communications base station is connected to a non-cellular telephone network.

19. The apparatus of claim 16, wherein the wireless transmitter or transceiver is configured to transmit the electrocardiographic data and the emergency alert message over a wireless communications network without the use of a dedicated communications base station at the user's residence.

20. The apparatus of claim 16, further configured to store baseline electrocardiographic information obtained using the apparatus in the processor-accessible memory of the apparatus.

\* \* \* \* \*